United States Patent [19]

Kaushansky et al.

[11] Patent Number: 5,545,536
[45] Date of Patent: Aug. 13, 1996

[54] COLONY-STIMULATING FACTOR DERIVATIVES

[75] Inventors: Kenneth Kaushansky, Bothell; Frederick S. Hagen, Seattle, both of Wash.

[73] Assignees: University of Washington; ZymoGenetics, Inc., both of Seattle, Wash.

[21] Appl. No.: 186,832

[22] Filed: Apr. 27, 1988

Related U.S. Application Data

[63] Continuation-in-part of Ser. No. 8,698, Jan. 29, 1987, abandoned.

[51] Int. Cl.[6] ................................ C12P 21/02
[52] U.S. Cl. ............... 435/69.1; 435/69.5; 435/91.32; 435/172.3; 435/254.21; 536/23.5; 530/350
[58] Field of Search .................. 435/68.1, 69.1, 435/69.5, 70.3, 91, 235, 320, 240.2, 255, 320.1, 256, 172.3, 91.1, 91.32; 536/27, 23.5; 530/350; 935/10, 32, 34, 57, 60, 70, 81

[56] References Cited

U.S. PATENT DOCUMENTS

| | | | |
|---|---|---|---|
| 5,032,676 | 7/1991 | Deeley et al. | 530/351 |
| 5,405,952 | 4/1995 | Deeley et al. | 536/23.5 |

OTHER PUBLICATIONS

Davis et al in Microbiology 2nd Edition, Harper & Row Publishers, Hegerstown, MD (1973) pp. 966–977.
Donahue et al Cold Spring Harbor Symposia on Quan Bio vol. 51 pp. 685–692 (1986).
Cantrell et al Proc Natl Acad Sci USA vol. 82 pp. 6250–6254 (1985).
Woang et al Science vol. 228 pp. 810–815 (1985).
De Lamarter et al EMBO vol. 4 pp. 2575–2581.
Miyajima et al EMBO vol. 5 pp. 1193–1197 (1986).
Leatherborrow et al Protein Engineering vol. 1 pp. 7–16 (1986).

*Primary Examiner*—Mary E. Mosher
*Assistant Examiner*—Laurie Scheiner
*Attorney, Agent, or Firm*—Seed and Berry

[57] ABSTRACT

Novel proteins possessing substantially the same biological activity as human GM-CSF, as well as proteins having a higher specific activity than native human GM-CSF, are disclosed. The proteins may (a) be unglycosylated; (b) lack N-linked glycosylation but have O-linked glycosylation; or (c) lack one of the two N-linked carbohydrate chains characteristic of native human GM-CSF. The proteins are produced using recombinant DNA techniques in eucaryotic host cells, such as mammalian, yeast, and filamentous fungal host cells. Pharmaceutical compositions including an effective amount of one of the proteins of the invention and a physiologically acceptable carrier or diluent are also disclosed.

6 Claims, 8 Drawing Sheets gmCSF N-Linked Sites Eliminated

```
 1                                                           10
ATG TGG CTG CAG AGC CTG CTG CTC TTG GGC ACT GTG GCC TGC AGC ATC TCT GCA
Met Trp Leu Gln Ser Leu Leu Leu Leu Gly Thr Val Ala Cys Ser Ile Ser Ala

20 gmCSF N- and O-Linked Sites Eliminated

```
1                                                   10
ATG TGG CTG CAG AGC CTG CTG CTC TTG GGC ACT GTG GCC TGC AGC ATC TCT GCA
Met Trp Leu Gln Ser Leu Leu Leu Leu Gly Thr Val Ala Cys Ser Ile Ser Ala 20                                  30
CCC GCC CGC GCA CCC GCA ACG CAG CCC TGG GAG CAT GTG AAT GCC ATC gmCSF one N-Linked Site Eliminated

```
1                                           10
ATG TGG CTG CAG AGC CTG CTG CTC TTG GGC ACT GTG GCC TGC AGC ATC TCT GCA
Met Trp Leu Gln Ser Leu Leu Leu Leu Gly Thr Val Ala Cys Ser Ile Ser Ala 20                                          30
CCC GCC CGC TCG CCC AGC CCC AGC ACG CAG CCC TGG GAG CAT GTG AAT GCC ATC
Pro Ala Arg Ser Pro Ser Pro Ser Thr Gln Pro Trp Glu His Val Asn Ala Ile 40                                          50
CAG GAG GCC CGG CGT CTC CTG CAA CTG AGT AGA GAC ACT GCT GCT GAG ATG AAT
Gln Glu Ala Arg Arg Leu Leu Gln Leu Ser Arg Asp Thr Ala Ala Glu Met Asn
                            ***

60                                          70
GAA ACA GTA GAA GTC ATC TCA GAA ATG TTT GAC CTC CAG GAG CCG ACC TGC CTA
Glu Thr Val Glu Val Ile Ser Glu Met Phe Asp Leu Gln Glu Pro Thr Cys Leu 80                                          90
CAG ACC CGC CTG GAG CTG TAC AAG CAG GGC CTG CGG GGC AGC CTC ACC AAG CTC
Gln Thr Arg Leu Glu Leu Tyr Lys Gln Gly Leu Arg Gly Ser Leu Thr Lys Leu

100
AAG GGC CCC TTG ACC ATG ATG GCC AGC CAC TAC AAG CAG CAC TGC CCT CCA ACC
Lys Gly Pro Leu Thr Met Met Ala Ser His Tyr Lys Gln His Cys Pro Pro Thr 110                                         120
CCG GAA ACT TCC TGT GCA ACC CAG ACT ATC ACC TTT GAA AGT TTC AAA GAG AAC
Pro Glu Thr Ser Cys Ala Thr Gln Thr Ile Thr Phe Glu Ser Phe Lys Glu Asn 130                                         140
CTG AAG GAC TTT CTG CTT GTC ATC CCC TTT GAC TGC TGG GAG CCA GTC CAG GAG
Leu Lys Asp Phe Leu Leu Val Ile Pro Phe Asp Cys Trp Glu Pro Val Gln Glu

TGA
```

*Figure 3*

COLONY-STIMULATING FACTOR DERIVATIVES

CROSS REFERENCE TO RELATED APPLICATION

This application is a continuation-in-part of U.S. Ser. No. 07/008,698, filed Jan. 29, 1987, now abandoned.

Portions of this work were supported by National Institutes of Health Grants CA-31615 and AI 22772.

TECHNICAL FIELD

The present invention relates to the production of proteins in general, and more specifically, to novel proteins having activities similar to human granulocyte macrophage colony-stimulating factor.

BACKGROUND ART

Colony-stimulating factors (CSFs) are acidic glycoproteins required for the survival, proliferation and differentiation of hematopoietic progenitor cells in culture (Burgess and Metcalf, *Blood* 56: 947–958, 1980). Functionally, the various CSFs are defined by the type of hematopoietic colony produced in semisolid culture. Hence, granulocyte-macrophage colony-stimulating factor (GM-CSF) stimulates the growth of progenitors which give rise to colonies containing granulocytes, macrophages, or a combination of both cell types (Wong et al., *Science* 228: 810–815, 1985). In addition to GM-CSF, granulocyte CSF (G-CSF or CSFβ), macrophage CSF (M-CSF or CSF-1) and multi-CSF (or IL-3) have been characterized and cloned from human sources (Souza et al., *Science* 232: 61–65, 1986; Kawasaki et al., *Science* 230: 291–296, 1985; Yang et al., *Cell* 47: 3–10, 1986).

The colony-stimulating factors are proteins of diverse physiologic function. Kaushansky et al. (*Proc. Natl. Acad. Sci. USA* 83: 3101–3105, 1986) and others (Emerson et al., *J. Clin. Invest.* 76: 1286–1290, 1985) have found that recombinant human GM-CSF (hGM-CSF) expressed in COS-1 cells stimulates not only neutrophilic, eosinophilic and monocyte-macrophage progenitor cells, but also megakaryocyte colony-forming cells and, in the presence of erythropoietin, erythroid and mixed erythroid-nonerythroid colony-forming cells. Further, hGM-CSF has been shown to stimulate mature neutrophils to localize at sites of inflammation (Weisbart et al., *Nature* 314: 361–363, 1985), mature eosinophils and monocytes to become activated and to enhance their killing of helminths (Handman and Burgess, *J. Immunol.* 122: 1134–1137, 1979; Vadas et al., *Blood* 61: 1232–1241, 1983), and mature monocytes and macrophages to enhance phagocytosis and tumor cell killing (Grabstein et al., *Science* 232: 506–508, 1986). In addition to these in vitro activities, recombinant hGM-CSF was recently demonstrated in primates to stimulate in vivo hematopoiesis (Donahue et al., *Nature* 321: 872–875, 1986).

Human GM-CSF is functionally distinguishable from human G-CSF or pluripoietin (Welte et al., *Proc. Natl. Acad. Sci. USA* 82: 1526–1530, 1985), human M-CSF (Kawasaki et al., *Science* 230: 291–296, 1985), also called CSF-1, and from human multi-CSF (Yang et al., *Cell* 47: 3–10, 1986), also known as IL-3. GM-CSF stimulates erythroid, eosinophilic, neutrophilic, monocytic and megakaryocytic cells, but does not stimulate mast cell colonies and is specific for human cells. In contrast, human M-CSF, a heterodimer of about 44 kDa, stimulates monocyte/macrophage colony formation almost exclusively; human G-CSF stimulates primarily the formation of neutrophilic but not eosinophilic colonies, stimulates erythroid and mixed erythroid/ non-erythroid colony formation only at a ten-folder higher concentration than is required for stimulation of granulocyte or granulocyte/macrophage colony formation, and also stimulates murine neutrophilic colony formation; and human multi-CSF stimulates mast cell colony formation.

Recombinant GM-CSF has been produced in several systems. Examples of such systems are found in the disclosures of (a) Golde et al. (U.S. Pat. No. 4,438,032), which describes the production of human GM-CSF in *E. coli* using a cDNA derived from the Mo cell line; (b) EP 183,350 and Grabstein et al. (ibid), which describe tile production of human GM-CSF in yeast; (c) PCT Application WO/8504188, which describes a cDNA-encoding murine GM-CSF which can be expressed in bacterial and mammalian host cells; and (d) PCT Application WO/8603225 and PCT Application 8600639, both of which describe the production of recombinant human GM-CSF in *E. coli* and other host cells.

Prior to the availability of recombinant human GM-CSF, many studies were conducted on the corresponding murine protein. Human and murine GM-CSFs are 60% homologous (Wong et al., ibid), but the mouse protein neither binds to nor stimulates human granulocyte or macrophage progenitor cells (Metcalf, *Science* 229: 16–22 1985). Murine GM-CSF has also been produced by Sparrow et al. (*Proc. Natl. Acad. Sci. USA* 82: 292–296, 1985) and DeLamarter et al. (*EMBO J.* 4: 2575–2581, 1985).

Despite the growing body of knowledge surrounding the in vitro, and now in vivo, physiology of hGM-CSF, little is known about the structural features responsible for the various functional properties of the growth factor. For example, CSFs are heavily glycosylated molecules. However, Donahue et al. (*Nature* 321: 872–875, 1986) studied unglycosylated GM-CSF produced in *E. coli* and concluded that the lack of carbohydrate had little effect on in vitro activity. In addition, Wong et al. (*Cancer Cells* 3: 235–241, Cold Spring Harbor Laboratory, New York, 1985) observed that natural and recombinant GM-CSFs exhibit varying molecular weights between 15 KD and 28 KD. They attributed this to differential carbohydrate addition or differential carbohydrate loss in purification, but detected no differences in specific activity or biological properties of the various fractions. Further, it has recently been reported that GM-CSF which lacks all carbohydrate failed to support erythroid progenitor cell proliferation (Burgess et al., *Blood* 84: 43–51, 1987).

The physiological role of the carbohydrate moieties of glycoproteins remains unclear. Ashwell and Morrell (*Adv. Enzymol. Relat. Areas Mol. Biol.* 41: 99–128, 1974) suggested a variety of functions for carbohydrate, including enhanced survival in the circulation, augmentation of binding to plasma proteins for transport, or enhancement of protein solubility. Hoffman et al. (*J. Clin. Invest.* 75: 1174–1182, 1985) found that deglycosylation of megakaryocyte colony stimulating factor by treatment with trifluoromethane sulfonate resulted in a loss of biological activity. Similarly, Sairam and Bhargavi (*Science* 229: 65–67, 1985) found that the carbohydrate moieties of the alpha subunit of glycoprotein hormones are involved in the transduction of the biological signal into cells.

In general, GM-CSF can be used within a variety of clinical applications where the proliferation of responsive cell types is desired. These applications include chemotherapy and bone marrow transplantation. However, in light of the uncertainty characteristic of the prior art, it would be advantageous to develop a more consistent method for producing proteins exhibiting activities similar to native human GM-CSF, and to develop such proteins which possess higher specific activity than the native molecule. The present invention fulfills this need, and further provides other related advantages.

DISCLOSURE OF THE INVENTION

Briefly stated, the present invention discloses a variety of unique proteins that possess substantially the same biological activity as human GM-CSF, as well as proteins that have a higher specific activity than native human GM-CSF. In one aspect of the present invention, the proteins are unglycosylated, while in another aspect, the proteins lack N-linked glycosylation but have O-linked glycosylation. In yet another aspect, the proteins lack one of the two N-linked carbohydrate chains characteristic of native human GM-CSF.

Within particular embodiments described hereinafter, proteins are disclosed having (a) the amino acid sequence of FIG. 1, starting with alanine, number 18, and ending with glutamate, number 144; (b) the amino acid sequence of FIG. 2, starting with alanine, number 18, and ending with glutamate, number 144; and (c) the amino acid sequence of FIG. 3, starting with alanine, number 18, and ending with glutamate, number 144. DNA sequences encoding these proteins are also disclosed.

In a related aspect of the present invention, methods are disclosed for producing the proteins described herein. Briefly, the methods comprise (a) introducing into a eucaryotic host cell an expression unit comprising a promoter followed downstream by a DNA sequence encoding one of the proteins disclosed herein; (b) growing the eucaryotic host cell in an appropriate medium; and (c) isolating the protein product encoded by the DNA sequence and produced by the eucaryotic host cell. Suitable eucaryotic host cells in this regard include mammalian, insect, yeast and filamentous fungal host cells.

Yet another aspect of the present invention discloses pharmaceutical compositions comprising an effective amount of one of the proteins described herein, and a physiologically acceptable carrier or diluent.

These and other aspects of the present invention will become evident upon reference to the following detailed description and attached drawings.

BRIEF DESCRIPTION OF THE DRAWINGS

FIG. 1 illustrates the amino acid sequence of a GM-CSF lacking N-linked carbohydrate, together with the nucleotide sequence encoding the protein. The mature protein begins with amino acid 18 (Ala). Asterisks indicate the locations of the altered codons.

FIG. 2 illustrates the amino acid sequence of a GM-CSF lacking N-linked carbohydrate and O-linked carbohydrate, together with the nucleotide sequence encoding the protein. The mature protein begins with amino acid 18 (Ala).

FIG. 3 illustrates the amino acid sequence and encoding nucleotide sequence of a GM-CSF lacking the N-linked carbohydrate at amino acid 44. The mature protein begins with amino acid 18 (Ala).

BEST MODE FOR CARRYING OUT THE INVENTION

Figure 4:
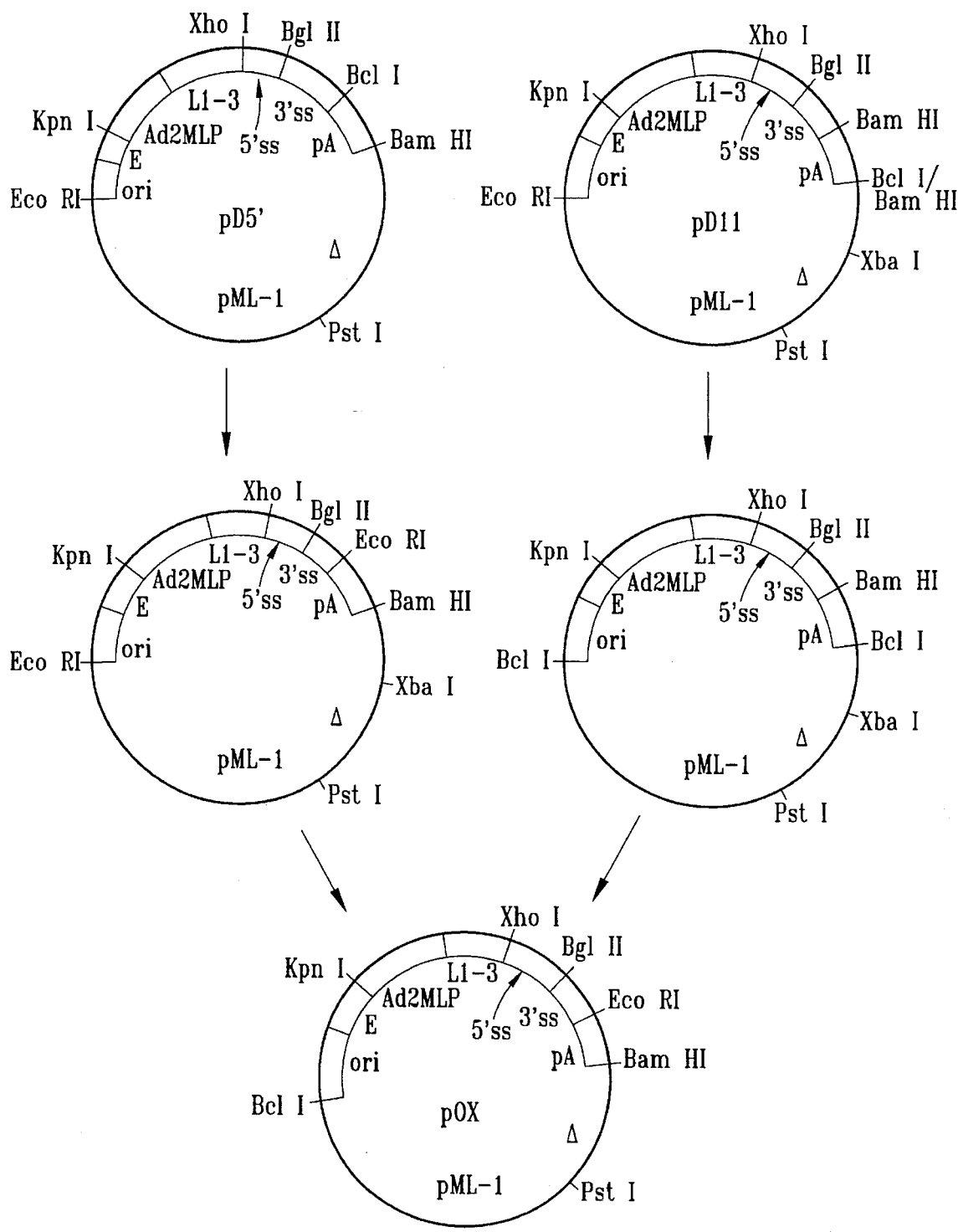
FIG. 4 illustrates the construction of the expression vector pDX. Symbols used are E, the SV40 enhancer; ori, the 0–1 map units from adenovirus 5; Ad2 MLP, the major late promoter from adenovirus 2; L1-3, the adenovirus 2 tripartite leader sequence; 5'ss, 5' splice site; 3'ss, 3' splice site; pA, the SV40 polyadenylation signal; , the deletion region of the pBR322 "poison" sequences.

Prior to setting forth the invention it may be helpful to an understanding thereof to set forth definitions of certain terms to be used hereinafter.

Biological Activity: A function or set of functions performed by a molecule in a biological context (i.e., in an organism or an in vitro facsimile). For human GM-CSF, biological activity is characterized by the stimulation of the proliferation and differentiation of certain hematopoietic progenitor cells. Human GM-CSF stimulates the formation of neutrophilic, eosinophilic, monocytic and megakaryocytic cells, as well as erythroid cells in the presence of erythropoietin.

Specific Activity: A quantitative description of the biological activity associated with a protein in terms of activity per unit mass. For native human GM-CSF, specific activity has been determined to be in the range of $4-8 \times 10^7$ units/mg. Within the present invention, the phrase "higher specific activity" is defined to include those proteins exhibiting a specific activity greater than about $4 \times 10^8$ units/mg.

Expression Unit: A DNA construct comprising a primary nucleotide sequence encoding a protein of interest, together with other nucleotide sequences which direct and control the transcription of the primary nucleotide sequence. An expression unit includes at least the primary nucleotide sequence and a promoter sequence located upstream from and operably linked to the primary nucleotide sequence. Additional genetic elements may also be included to enhance efficiency of expression. These elements include a transcription terminator, a polyadenylation signal, enhancer sequences, leaders, and RNA splice sites.

The novel proteins of the present invention can be used in various clinical applications where the proliferation of responsive cell types is desired. These applications include chemotherapy, where recovery from cytoxic drug-induced leukopenia may be speeded through the use of these proteins, which may allow more intensive use of such therapy. Treatment with these proteins may also permit more frequent use of myelotoxic drugs, speed recovery from bone marrow ablation during marrow transplantation and improve leukocyte production in states of marrow hyperproliferation, such as aplastic anemia. Furthermore, neutrophil production in persons being utilized as white blood cell donors may be enhanced. These proteins may also be used to enhance nonspecific host defense mechanisms in patients with overwhelming bacterial, fungal or parasitic infections, or in patients with non-responsive cancers. Certain proteins of the present invention are even more advantageous over the naturally-occurring GM-CSF due to their higher specific activities. This enhanced activity may allow the use of less material per patient per dose, which can be expected to reduce undesirable side effects, such as capillary leak syndrome, which has been observed with therapeutic use of recombinant native GM-CSF (Brandt et al., *Blood* 70, Suppl. 1, 131a, 1987.

For administration to patients, the purified proteins of the present invention are mixed with a pharmaceutically acceptable carrier or diluent in accordance with routine procedures. Typically, such compositions will comprise a solution in sterile 5% dextrose or physiological saline and will be tested for sterility and verified to be free of endotoxin contamination, e.g., by the Limulus amoebocyte assay system. Therapeutic formulations will be administered by intravenous infusion or by subcutaneous injection. The formulations can also contain, if desired, other therapeutic agents. Dosages will be determined based upon the characteristics of the patient and the nature and severity of the condition being treated, as will be evident to and within the skill of those in the art.

Most previous attempts at producing unglycosylated GM-CSF have relied on the use of prokaryotic host cells which add neither N-linked nor O-linked glycosylation. The resultant proteins therefore contain an extra amino-terminal methionine residue. This methionine may be recognized as foreign by the human body or may otherwise affect the activity of the protein. In contrast, the present invention provides an unglycosylated protein or a protein lacking N-linked glycosylation but having O-linked glycosylation, or a protein lacking one of the two N-linked carbohydrate chains characteristic of native human GM-CSF, the proteins being produced in transfected mammalian cells. These proteins have the biological activity of natural human GM-CSF, and may have a higher specific activity. Furthermore, the proteins of the present invention do not have an amino-terminal methionine.

The proteins of the present invention are produced by expressing mutagenized DNA sequences in transfected or transformed host cells.

cDNA sequences encoding GM-CSF may be obtained from cDNA libraries by conventional procedures (e.g., that of Wong et al., ibid). Alternatively, the cDNA may be obtained as described herein from transfected mammalian cells expressing the cloned human GM-CSF gene. A human GM-CSF genomic clone is disclosed by Kaushansky et al. (ibid). Such cells are a rich source of GM-CSF-specific mRNA. By removing the translation initiation and stop signals upstream of the sequence coding for the amino terminal residues of hGM-CSF, biologically active protein was expressed from the intact gene at high levels using an SV40 ori-based expression system in COS-1 (African green monkey kidney) cells. When compared directly by Northern blot analysis, transiently expressing COS-1 cells have approximately ten times higher levels of GM-CSF-specific mRNA than lectin-stimulated lymphocytes and are thus a rich source of such mRNA. When a λgt11 cDNA library was prepared from the mRNA of these COS-1 cells, it was found that approximately 0.1% of the independent recombinant cDNA clones in this library were hGM-CSF-specific. All of the clones assessed demonstrated proper intron splicing, and all of the clones sequenced contained a complete copy of hGM-CSF cDNA. Finally, the cDNA directed the synthesis of higher levels of biologically active hGM-CSF, as compared to the genomic DNA.

Once a complete cDNA for hGM-CSF was obtained, site-directed mutagenesis (Zoller and Smith, *DNA* 3: 479–488, 1984) was used to alter the sequence. A double mutant was generated in a single reaction, resulting in cDNA coding for a polypeptide which could no longer be N-glycosylated at either naturally-occurring site. Additional mutagenesis generated mutants which could no longer be O-glycosylated and mutants which lacked both forms of carbohydrate. Single glycosylation sites may also be removed individually. By altering the Asn residues at the N-linked glycosylation sites (sequence Asn-X-Ser/Thr, wherein X is any amino acid) to another amino acid residue, glycosyation may be blocked. It is particularly preferred that the Asn residues be changed to Gln residues. Asn may also be changed to Set or Thr. Additionally, other alterations in the sequence may be introduced for the purpose of blocking glycosylation of the encoded protein. For example, a proline residue in the second position of the sequence Asn-X-Ser/Thr may prohibit glycosylation (Marshall, *Blochem. Soc. Symp.* 40: 17–26, 1974). Other substitutions may also be made at this position. The third amino acid of an N-linked glycosylation site may also be changed, preferably to Ala, Cys, Gly, Asn or Gln. O-linked carbohydrate chains are linked to a serine or threonine residue, which is usually flanked by proline. O-linked glycosylation can be blocked by substituting another amino acid, preferably alanine, for the serine or threonine, or by substituting another amino acid for the flanking proline.

Because the carbohydrate portion(s) of glycoproteins may contribute to survival of those proteins in the circulation, it may in some instances be preferred to retain some of the carbohydrates. The inventors have found, for instance, that where the O-linked carbohydrate is retained on a protein which lacks N-linked carbohydrate, the resultant protein has the enhanced activity of the fully unglycosylated protein and may have enhanced survival in circulation. In addition, retention of a single N-linked carbohydrate side chain may enhance the efficiency of production of the protein in recombinant cell culture. Thus, a molecule altered so as to retain only O-linked carbohydrate or O-linked carbohydrate and one N-linked carbohydrate may provide significant advantages over both the native GM-CSF and the fully unglycosylated protein.

The mutagenized cDNA sequences were then inserted into an expression vector and expressed in transfected COS-1 (ATCC CRL 1650) cells. Other cultured mammalian cell lines, including the BHK (ATCC CCL 10), 293 (ATCC CRL 1573), CHO (ATCC CCL 61), J558L (ATCC TIB 6) and BHK tk⁻ ts 13 (Waechter and Baserga, *Proc. Natl. Acad. Sci. USA* 79: 1106–1110, 1982) cell lines, as well as other types of host cells, may also be used.

Expression vectors or expression units for use in mammalian cells include a promoter capable of directing the transcription of a cloned gene introduced into a mammalian cell. Particularly preferred promoters include the SV40 (Subramani et al. *Mol. Cell Biol.* 1: 854–64, 1981), MT-1 (Palmiter et al., *Science* 222: 809–814, 1983), and adenovirus 2 major late promoters. The expression vectors may also contain a polyadenylation signal, located downstream of the insertion site for the DNA sequence to be expressed. Vital polyadenylation signals are preferred, such as the early or late polyadenylation signals from SV40 or the polyadenylation signal from the adenovirus 5:EIb region. Expression vectors may also include RNA splice sites and a vital leader sequence, such as the adenovirus 2 tripartite leader, located between the promoter and the RNA splice sites. Preferred vectors may also include enhancer sequences, such as the SV40 enhancer.

Cloned DNA sequences may then be introduced into cultured mammalian cells by calcium phosphate-mediated transfection (Wiglet et al., *Cell* 140: 725, 1978; Corsaro and Pearson, *Somatic Cell Genetics* 7: 603, 1981; Graham and Van der Eb, *Virology* 52: 456, 1973) or electropotation (Neumann et al., *EMBO J.* 1: 841–845, 1982). A portion of the cells take up the DNA and maintain it inside the cell for several days. A small fraction of the cells (typically 1 in $10^4$ cells) integrate the DNA into the genome or maintain the DNA in non-chromosomal nuclear structures. In order to identify these integrants a gene that confers a selectable phenotype (a selectable marker) is generally introduced along with the gene of interest. Preferred selectable markers include genes that confer resistance to drugs, such as G-418 and methotrexate. Selectable markers may be introduced into the cell on a separate plasmid at the same time as the gene of interest or they may be introduced on the same plasmid. A preferred selectable marker is the gene for resistance to the drug methotrexate. It may also be advantageous to add additional DNA, known as "carrier DNA," to the mixture which is introduced into the cells. After the cells have taken up the DNA, they are allowed to grow for a period of time, typically 1–2 days, to begin expressing the gene of interest. Drug selection is then applied to select for the growth of cells which are expressing the selectable marker in a stable fashion. Clones of such cells may be screened for expression of the protein of interest.

Eukaryotic microorganisms, such as the yeast *Saccharomyces cerevisiae* or filamentous fungi, including Aspergillus, may also be used as host cells. Particularly preferred species of Aspergillus include *A. nidulans, A. niger, A. oryzae,* and *A. terreus*. Techniques for transforming yeast are described by Beggs (*Nature* 275: 104–108, 1978). Expression vectors for use in yeast include YRp7 (Struhl et al., *Proc. Natl. Acad. Sci. USA* 76: 1035–1039, 1979), YEp13 (Broach et al., *Gene* 8: 121–133, 1979), pJDB248 and pJDB219 (Beggs, ibid), and derivatives thereof. Such vectors will generally comprise a selectable marker, such as the nutritional marker TRP, which allows selection in a host strain carrying a trp1 mutation. Preferred promoters for use in yeast expression vectors include promoters from yeast glycolytic genes (Hitzeman et al., *J. Biol. Chem.* 255: 12073–12080, 1980; Alber and Kawasaki, *J. Mol. Appl. Genet.* 1: 419–434, 1982; Kawasaki, U.S. Pat. No. 4,599, 311) or alcohol dehydrogenase genes (Young et al., in *Genetic Engineering of Microorganisms for Chemicals,* Hollaender et al., eds., p. 335, Plenum, New York, 1982; and Ammerer, *Meth. in Enzymology* 101: 192–201, 1983). To avoid the presence of an N-terminal methionine residue, facilitate purification and avoid potential toxic effects of the foreign protein on the yeast cells, it is preferred that a signal sequence from a yeast gene encoding a secreted protein be included in the expression vector. A particularly preferred signal sequence is the pre-pro region of the MF α1 gene (Kurjan and Herskowitz, *Cell* 30: 933–943, 1982). Signal sequences may also be obtained from other yeast genes such as PHO5 (International Patent Application WO/8600637) and the gene encoding a-factor (EP 123,289). Aspergillus species may be transformed according to known procedures, for example, that of Yelton et al. (*Proc. Natl. Acad. Sci. USA* 81: 1740–1747, 1984).

The proteins of the present invention are preferably isolated from the host cell culture media by immunoaffinity chromatography followed by HPLC, although other conventional techniques may be employed. Purification may be monitored using dot blot assays or radio-immune assays which utilize anti-GM-CSF antiserum, and activity may be assayed by bone marrow colony-forming assays. Product purity is preferably assessed by SDS polyacrylamide gel electrophoresis with silver staining and amino acid sequence analysis.

The mutated cDNAs were transcribed in cultured COS-1 cells at levels similar to the wild-type cDNA, and the recombinant polypeptides produced were demonstrated to lack terminal mannose residues by chromatography over concanavalin A agarose. When the relative specific activities of the mutant recombinant proteins were assessed in vitro, it was found that polypeptides lacking N-linked carbohydrate had approximately six-fold higher specific activity. The functional properties of the recombinant mutant proteins were then compared to those of the native growth factor. Using whole agar cultures and cytochemistry, the distribution of cell types stimulated by the native and non-glycosylated forms of hGM-CSF were shown to be similar. Furthermore, by dose-response analysis, both forms were equally able to stimulate the growth of megakaryocyte colonies and, in the presence of erythropoietin, erythroid bursts. In addition, in vivo studies demonstrated that certain of the mutant proteins had increased plasma half lives.

From these studies, it is clear that carbohydrate addition is not necessary to allow the full range of progenitor cell stimulation provided by native hGM-CSF in vitro. In addition, the recombinant proteins lacking N-linked carbohydrate were able to inhibit the migration of mature neutrophils toward the chemoattractant fMet-Leu-Phe.

The following examples are offered by way of illustration and not by way of limitation.

EXAMPLES

Example 1—Cloning of GM-CSF cDNA

A genomic clone encoding human GM-CSF (hGM-CSF) was obtained as described by Kaushansky et al. (*Proc. Natl. Acad. Sci. USA* 83: 3101–3105, 1986). Briefly, a once-amplified λCharon 4A phage library of human genomic DNA was screened using a 70 base oligonucleotide probe derived from the murine and human GM-CSF amino acid sequences. Positive clones were plaque-purified and analyzed by restriction analysis and plaque hybridization. Three clones were found to hybridize to additional probes to the 5' and 3' ends of human GM-CSF cDNA (Wong et al., ibid). These clones were found to be identical and were designated AhGM-CSF.

The GM-CSF genomic clone was then subcloned into the mammalian cell expression vector pD5' and used to transfect cultured COS-1 cells. pD5' is an SV40 ori-based plasmid vector that permits the expression of exogenous genomic and cDNA fragments under the control of the adenovirus major late promoter. pD5' also comprises an adenovirus tripartite leader sequence, an SV40 enhancer, the polyadenylation signal derived from adenovirus, and a unique Bcl I cloning site in the vector pML-1 (Lusky and Botchan, *Nature* 293: 79–81, 1981). The construction of pD5' is described in Example 4.

To prepare the expression vector, the 2.6 kb Bst EII/Eco RI fragment from λhGM-CSF, containing only the region from the TATA box to the polyadenylation signals, was subcloned into the Bcl I site of pD5' and used to transfect COS-1 cells (Graham and Van der Eb, *Virology* 52: 456, 1973) The three-day COS-1 cell supernatants were assayed for biologically active hGM-CSF by standard human bone marrow culture (Kaushansky et al., ibid). The expression vector, designated pDgGMII, directed production of 1.9–2.9×10$^4$ U/ml hGM-CSF.

Poly A-containing RNA was prepared from transfected COS-1 cell RNA by chromatography over oligo dT cellulose. Double stranded cDNA was prepared by a modification of the RNase H/DNA polymerase I method (Gubler and Hoffman, *Gene* 25: 263–269, 1983) adapted to the production of a λgt11 phage library. Five ug of poly (A)+RNA were used to prepare 2.5 ug of first strand cDNA by reverse transcriptase using oligo dT priming. RNAse H and DNA polymerase were used to synthesize second strand cDNA. After blunt- ending the cDNA molecule with T$_4$ DNA polymerase, 2 ug of double-stranded cDNA were ligated to an equal mass of Eco RI linkers. The reactants were digested with Eco RI and the cDNA was separated from linker monomers by gel filtration chromatography. 560 ng of cDNA was recovered from the void volume of the column. cDNA was ligated to an equimolar amount of λgt11 which had been prepared by digestion with Eco RI and treated with calf alkaline phosphatase. The DNA in the ligation mix was packaged using a λ phage packaging extract.

Of the 5×10$^5$ recombinants prepared from 37 ng of cDNA, 3×10$^5$ were screened. Phage were transferred to nitrocellulose and prehybridized (Ullrich et al., *EMBO J.* 3: 361–364, 1980). The filters were hybridized with 10$^6$ cpm/ml of a nick-translated 540 bp Sst I human GM-CSF genomic fragment as probe and washed in 0.2×SSC, 0.1% SDS at 65° C. for 60 minutes. Overall, 248 plaques hybridized strongly with the nick-translated genomic probe under the very stringent wash conditions used, suggesting that approximately 0.1% of the clones contained cDNA for hGM-CSF.

Six cDNA clones were plaque-purified and phage DNA was prepared from liquid cultures (Maniatis et al., *Cell 15: 687–701, 1978*) and subcloned into the Eco RI site of pUC13. One plasmid was selected and designated pUCcGM. The cloned cDNAs were also subcloned into M13mp18 and M13mp19 for sequencing by the dideoxynucleotide chain termination method (Sanger et al., *Proc. Natl. Acad. Sci. USA* 74: 5463–5467, 1977). All six clones contained a single open reading frame and their sequences matched that previously published (Wong et al., ibid; Lee et al., *Proc. Natl. Acad. Sci. USA* 82: 4360–4364, 1985) for human GM-CSF cDNA clones.

One cDNA was subcloned into the mammalian expression vector pDX and used to transiently express hGM-CSF. Expression vector pDX was derived from pD5' as described in Example 4B. A 593 bp Sst I/Nco I fragment from the cap site to the middle of the 3' untranslated region containing the entire GM-CSF coding sequence was removed from pUC-cGM. The cDNA restriction fragment was blunted with T$_4$ polymerase, ligated to Eco RI linkers, digested with Eco RI and subcloned into the unique Eco RI site of pDX. The resultant plasmid was designated pDcGMI. Plasmid DNA was transfected into COS-1 cells by calcium phosphate precipitation (Graham and Van der Eb, ibid). Culture medium (Dulbecco's modified essential medium, supplemented with antibiotics and either 10% fetal calf serum [FCS] or a serum-free supplement containing 1 ug/ml fibronectin, 10 ug/ml transfertin, 5 ug/ml insulin and 15 nM selenous acid [Collaborative Research]) conditioned by the transfected COS-1 cells was harvested after 3 days of incubation at 37° C. under 7% $CO_2$ and assayed for biologically active GM-CSF as described in Example 3.

The serum-free supernatants from COS-1 cells transiently expressing the native or mutant GM-CSF cDNAs were concentrated by ultrafiltration and applied slowly to 5 ml columns of concanavalin A agarose (1 cm ×7 cm) previously equilibrated with 20 mM Tris pH 7.4, 150 mM NaCl, 1 mM $MnCl_2$, 1 mM $CaCl_2$, and 1 mM $MgCl_2$. The columns were washed with 5 column volumes of the same buffer and bound glycoproteins were eluted with buffer containing 0.4 M α-methylmannoside (αMM). Samples were dialyzed against several changes of PBS and assayed for biologically active hGM-CSF as described in Example 3. When compared to the genomic expression vector pDgGMII, the cDNA directed the synthesis of 4-fold more recombinant hGM-CSF, or about 1×10$^5$ U/ml of serum-containing culture medium.

Example 2—Site-Specific Mutagenesis

The human GM-CSF cDNA was modified by site-directed in vitro mutagenesis (Zoller and Smith, *DNA* 3: 479–488, 1984) to remove the five glycosylation sites, Plasmid pUCcGM, containing the human GM-CSF cDNA, was cut with Eco RI to isolate the 0.9 kb cDNA insert. This fragment was ligated into M13mp18, which had been linearized by digestion with Eco RI. Site-directed in vitro mutagenesis (Zoller and Smith, ibid) was performed on the resultant phage (M13cGMI) using oligonucleotides synthesized on an Applied Biosystems model 380A DNA synthesizer and purified by polyacrylamide gel electrophoresis on denaturing gels. The mutagenesis to change the N-linked glycosylation sites at amino acids 44 and 54 (amino acids are numbered as shown in FIGS. 1–3) was carried out using oligonucleotide ZC556 ($^5$'GCGTCTCCTGCAACTGAG-TAGAG$^3$') to change the asparagine at amino acid 44 to glutamine and oligonucleotide ZC555 ($^5$'TGCTGAGATG-CAAGAAACAGTAG$^3$') to change the asparagine at amino acid 54 to glutamine together with the oligonucleotide primer ZC87 ($^5$'TCCCAGTCACGACGT$^3$'). The double mutants were screened by probing plaques with each $^{32}$p end-labelled oligonucleotide using wash conditions stringent enough (3M tetramethylammonium chloride [TMACl] at 62° C.) to allow only 21 or 22 base matches to retain a hybridization signal (Wood et al., *Proc. Natl. Acad. Sci. USA* 82: 1585–1588, 1985). Approximately 60 phage hybridized to either probe independently, while only three hybridized to both probes. Positive clones were sequenced from the translation start site through the mutagenized sites to confirm the mutations. The positive clone was designated M13-555-556. To remove O-linked glycosylation sites, phage M13-555-556 and M13cGMI were subjected to site-directed in vitro mutagenesis using oligonucleotide ZC867 ($^5$'ACCCGC-CCGCGCACCCGCACCCGCAACGCAGCCCT$^3$') to change the serine codons found at positions 22, 24 and 26 to alanine codons. The mutagenized phage were screened as described above with washing at 75° C. in 3M TMACl. In this way, mutant cDNA clones which contain only O-linked, only N-linked or none of the known carbohydrate addition sites were generated. Positive clones were sequenced from the translation start site through the mutagenized sites to confirm the mutations. The clone containing all five mutagenized sites was designated M13-555-556-867, that containing only O-linked sites was designated M13-555-556 and the clone containing only N-linked sites was designated M13-867.

Replicative form DNA was made from the phage clones M13-555-556, M13-555-556-867 and M13-867. The DNA was cut with Eco RI to isolate the 0.9 kb fragments from each phage clone. The 0.9 kb fragment isolated from M13-555-556 was ligated into pUC13 linearized by digestion with Eco RI to generate plasmid pUCcGM$_{555-556}$. The 0.9 kb fragment isolated from M13-555-556-867 was ligated into pUC13 linearized by digestion with Eco RI to generate plasmid pUCcGM$_{555-556-867}$. The 0.9 kb fragment from M13-867 was inserted into pUC13 to construct pUCcGM867. As these plasmids contained 211 base pairs of pD3-derived sequences upstream of the GM-CSF coding region, the plasmid-derived sequences were removed by cutting with Sst I, blunting with $T_4$ DNA polymerase, ligating to Eco RI linkers and cutting with Eco RI. The resultant fragments were subcloned into pDX to produce pDcGMII (–N), pDcGMIII (–O), and pDcGMIV (–N, –O). The mutagenized DNA sequences and the encoded amino acid sequences are shown in FIG. 1 (–N) and FIG. 2 (–O, –N). Subsequent analysis showed that mutant GM-CSFs III and IV contained an O-linked site at threonine number 11. This site was found to be glycosylated in about 50% of the recombinant protein molecules.

To determine if biologically active hGM-CSF was expressed by the altered cDNAs, pDcGMII, pDcGMIII and pDcGMIV were transfected separately into parallel cultures of COS-1 cells and compared to control transfections with pDcGMI. RNA was obtained from cells two days later and culture media were obtained from separate cultures after three days. The GM-CSF-specific mRNA levels were shown to be equivalent for all cDNA species, but varying amounts of biologically active recombinant GM-CSF were detected by bioassay.

In a similar manner, the N-linked glycosylation site at Asn 44 was removed. Phage M13cGMI was mutagenized using oligonucleotides ZC556 and ZC87. The resultant phage clone was designated M13-556.

Replicative form DNA was prepared from M13-556 and the altered GM-CSF sequence was subcloned into pDX as described above. The resultant expression vector was designated pDcGMV. The sequences of the cDNA insert and the encoded protein are shown in FIG. 3.

Example 3—Analysis of Proteins

To biochemically demonstrate the elimination of carbohydrate in the mutant polypeptides, the recombinant human GM-CSF preparations were analyzed by affinity chromatography. Serum-free COS-1 cell supernatants were applied to a concanavalin A agarose column. A 2 ml column (6 mm ×80 mm) of concanavalin A agarose was equilibrated in 20 mM Tris pH 7.5/150 mM NaCl/1 mM CaCl$_2$/1 mM MgCl$_2$/1 mM MnCl$_2$. Media conditioned by COS-1 cells transiently expressing the cDNA for native human GM-CSF or the modified GM-CSFs was applied slowly (0.2 ml/min) and the column was washed with equilibration buffer. Material bound to the column was eluted with 0.4M α-methylmannoside in equilibration buffer. The starting material, pass-through, wash, and elution fractions were dialyzed against PBS, filter-sterilized, and assayed for GM-CSF by colony formation. As shown in Table I, significant amounts of native GM-CSF and protein which no longer contains O-linked carbohydrate bound to concanavalin A agarose and could be eluted from the column. In contrast, both mutant GM-CSF species lacking N-linked carbohydrate failed to bind to concanavalin A agarose, and no growth factor could be eluted from the column. Results in Table I are expressed as the percentage of units applied recovered in the pass and wash and in the eluted fractions.

TABLE I

| Medium | Non-Bound | Bound and Eluted |
|---|---|---|
| pDcGMI (native) | 70 | 30 |
| pDcGMII (—N) | 100 | 0 |
| pDcGMIII (—O) | 71 | 29 |
| pDcGMIV (—N—O) | 100 | 0 |

Figure 5:
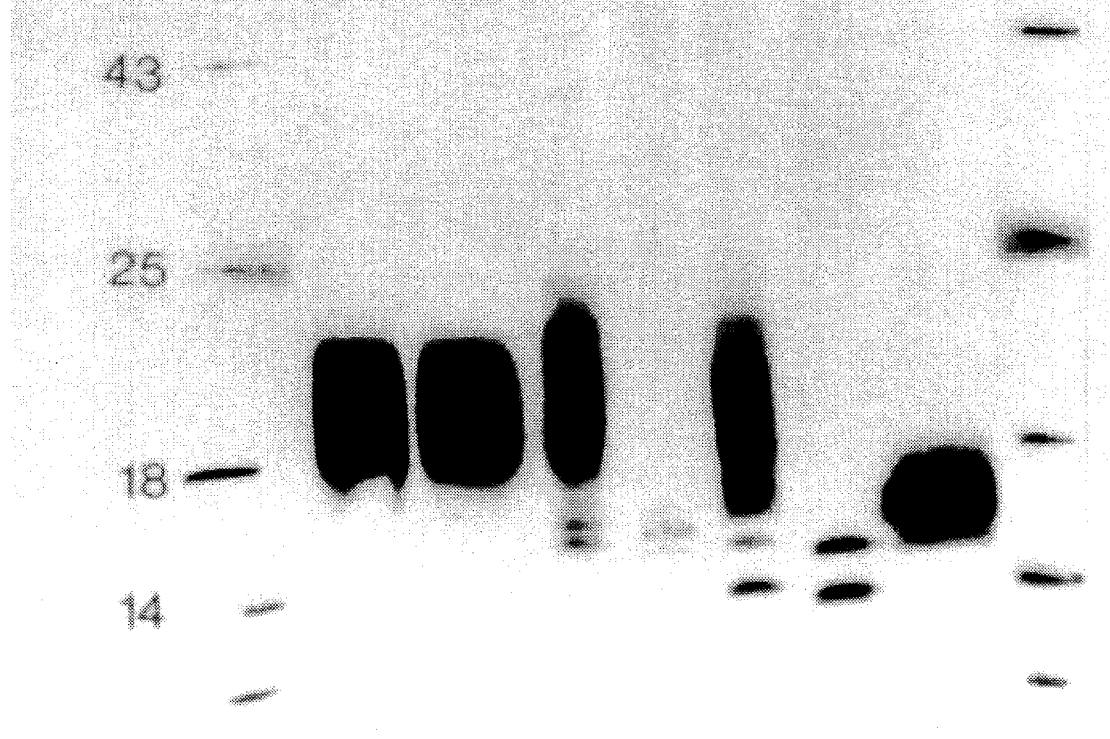
FIG. 5 shows a Western blot of native and mutant forms of recombinant human GM-CSF produced in COS-1 cells. Proteins were size-fractionated by SDS-PAGE, transferred to nitrocellulose, probed with a human GM-CSF-specific antiserum, and developed with a goat anti-rabbit biotin-avidin-peroxidase complex. Lane 1, HPLC-purified native GM-CSF; lane 2, native GM-CSF; lane 3, GM-CSF lacking N-linked carbohydrate; lane 4, GM-CSF lacking O-linked carbohydrate; lane 5, GM-CSF lacking all carbohydrate; lane 6, GM-CSF from which carbohydrate was removed by enzymatic means; lane 7, molecular weight markers. All lanes contain an equal number of biologically active units of GM-colony-stimulating activity except lane 3, which contains one-half as many units.

Next, to assess the relative specific activities of the various forms of GM-CSF produced by the mutant expression vectors, the conditioned media were analyzed immunologically. A rabbit antiserum was raised against a 15 residue synthetic peptide coupled to keyhole limpet hemocyanin. This antiserum recognizes a region of GM-CSF far removed from the carbohydrate addition sites. The antiserum binds as intensely to highly purified native GM-CSF as to the same amount of protein from which the carbohydrate has been removed enzymatically. Using this antiserum, the recombinant mutant and native proteins present in equal biologically active amounts of medium conditioned by transfected COS-1 cells were analyzed. As shown in FIG. 5, significantly less immunoreactive protein accounts for this activity in the polypeptides which lack N-linked carbohydrate than in the native form of hGM-CSF. O-linked carbohydrate does not affect the relative specific activity of these proteins to a significant degree. Finally, to quantitate these findings, serial dilutions of conditioned media were analyzed by Western blots using $^{125}$I goat anti-rabbit antiserum as a second antibody. After autoradiography, the hybridizing proteins were cut from the blot and counted. Six-fold greater amounts of hematopoietic activity were present in the two N-linked carbohydrate-deficient growth factors than in an immunoreactive equivalent amount of native GM-CSF. Given that native human GM-CSF has a specific activity of approximately $8 \times 10^7$ units/mg, the N-linked carbohydrate-deficient forms of the protein have specific activities in excess of $4 \times 10^8$ units/mg.

Functional Analysis of Recombinant Proteins

Limiting dilutions of serum-free COS-1 cell supernatants were assayed for their ability to stimulate granulocyte and/or macrophage colony growth in semisolid culture. In five separate experiments, there were no significant differences between the maximal number of granulocyte and macrophage (GM) colonies produced by the native and the mutant forms of recombinant human GM-CSF. When the GM colonies were evaluated for cell type by cytochemistry, a similar distribution of neutrophils, eosinophils and monocyte-macrophage containing colonies developed (Table II). Bone marrow cells were prepared as described (Bagby et al., J. Clin. Invest. 68: 56–63, 1981), except they were made semisolid with 0.3% agar. Whole cultures were fixed, stained for chloroacetate esterase and counterstained with toluidine blue. The data represent the results of triplicate plates containing a total of over 200 colonies for each form of GM-CSF and are expressed as the percentage of colonies containing each cell type. There were no significant differences when cultures were stimulated with varying concentrations of recombinant growth factor, or when colony size or cellular composition were analyzed.

TABLE II

| Cell Type | Medium: | | | |
|---|---|---|---|---|
| | pDcGMI Native | pDcGMII (—N) | pDcGMIII (—O) | pDcGMIV (—N—O) |
| Experiment 1 | | | | |
| Neutrophil | 67 | 71 | | |
| Eosinophil | 17 | 16 | | |
| Monocyte | 56 | 52 | | |
| Experiment 2 | | | | |
| Neutrophil | 55 | | 43 | 51 |
| Eosinophil | 40 | | 47 | 44 |
| Monocyte | 32 | | 29 | 39 |

Finally, both the mutant and the native recombinant proteins were capable of supporting the growth of megakaryocyte colonies and erythroid bursts. Spent culture media from transfected COS-1 cells were plated at 1% final concentration in bone marrow colony-forming assays. Controls include sham transfected COS-1 cell-conditioned medium and 1% PHA stimulated lymphocyte-conditioned medium (PHA-LCM). As shown in Table III, concentrations of either recombinant native or mutant unglycosylated GM-CSF which would half-maximally stimulate GM colony formation were equal in their ability to maximally stimulate the growth of megakaryocyte colonies and erythroid bursts. The data in a represent the mean number of colonies formed (±SEM) in a typical experiment plated in triplicate, and have been reproduced three times.

TABLE III

| Medium | Colony Number* | | |
|---|---|---|---|
| | Granulocyte-Macrophage | Erythroid Bursts | Megakaryocytes |
| Sham transfected | | | |
| COS-1 CM | 3.0 ± 1.1 | 3.4 ± 0.9 | 0 |
| PHA-LCM | 43.0 ± 3.0 | 28.0 ± 2.0 | 2.0 ± 0 |
| Native cDNA | 29.0 ± 3.0 | 26.0 ± 1.0 | 3.3 ± 0.7 |
| Mutant cDNA | | | |
| pDcGMII (—N) | 31.0 ± 5.0 | 29.0 ± 4.0 | 2.3 ± 0.9 |
| pDcGMIII (—O) | 29.0 ± 3.0 | 19.0 ± 3.0 | N.D. |
| pDcGMIV (—N—O) | 36.0 ± 2.0 | 22.0 ± 2.0 | N.D. |

*N.D. = not done

Biological Assay for GM-CSF

Bone marrow cells, obtained from normal human volunteers with their informed consent, were fractionated on a Ficoll-hypaque density gradient (sp. gravity 1.077). Low density cells were depleted of adherent cells by double plastic adherence and of T cells by E-rosetting (Bagby et al., *J. Clin. Invest.* 68: 56–63, 1981). Fifty to one hundred thousand cells were cultured in α medium in the presence of 15% fetal calf serum (FCS), antibiotics, 0.9% methylcellulose, and up to 10% of the material to be assayed. Cultures were incubated for 13 days in a humidified atmosphere containing 5% $CO_2$ and granulocyte-macrophage colonies were enumerated by inverted microscopy. Each experiment described represents the mean of triplicate cultures. Fifty units (U) of human GM-CSF is defined by the dilution which stimulates half-maximal colony formation, compared to an optimal concentration of phytohemagglutinin- stimulated lymphocyte conditioned medium (PHA-LCM). For the growth of megakaryocyte colonies, 25% human plasma was substituted for FCS (Kimura et al., *J. Cell Physiol.* 118: 87–96, 1984), and for the growth of erythroid bursts and mixed cell colonies (Powell et al., *Br. J. Haematol.* 51: 81–89, 1984), one unit of recombinant erythropoietin (Amgen, Inc.) was added on day 4 of culture. Optimal stimulation was provided by 1% PHA-LCM. For morphological analysis, cultures were made semisolid with 0.3% agar, fixed and stained for chloroacetate esterase and counterstained with toluidine blue. The colonies were enumerated and scored by direct microscopy.

Example 4A—Construction of pD5

Plasmid pD5, which comprises the SV40 enhancer and the adenovirus 2 major late promoter and tripartite leader, was generated from plasmid pDHFRIII (Berkner and Sharp, *Nuc. Acids Res.* 13: 841–847, 1985). The Pst I site immediately upstream from the DHFR sequence in pDHFRIII was converted to a Bam HI site by digesting 10 ug of plasmid with 5 units of Pst I for 10' at 37° C. in 100 ul buffer A (10 mM Tris pH 8, 10 mM $MgCl_2$, 6 mM NaCl, 7 mM -MSH). The DNA was phenol extracted, EtOH precipitated, and resuspended in 40 ul buffer B (50 mM Tris pH 8, 7 mM $MgCl_2$, 7 mM -MSH) containing 10 mM dCTP and 16 units $T_4$ DMA polymerase and incubated at 12° C. for 60 minutes. Following EtOH precipitation, the DNA was ligated to 2.5 ug kinased Bam HI linkers in 14 ul buffer C (10 mM Tris pH 8, 10 mM $MgCl_2$, 1 mM DTT, 1.4 mM ATP) containing 400 units $T_4$ polynucleotide ligase for 12 hours at 12° C. . Following phenol extraction and EtOH precipitation, the DMA was resuspended in 120 ul buffer D (75 mM KCl, 6 mM Tris pH 7.5, 10 mM $MgCl_2$, 1 mM DTT), digested with 100 units Bam HI for 60 minutes at 50° C., then electrophoresed through agarose. The 4.9 kb DMA fragment containing pBR322 and vector sequences (10 ug) was isolated from the gel, and ligated in 10 ul buffer C containing 50 units $T_4$ polynucleotide ligase for 2 hours at 12° C., and used to transform *E. coli* HB101. Positive colonies were identified by rapid DMA preparation analysis, and plasmid DMA (designated pDHFR') was prepared.

Plasmid pD1 was then generated by first cleaving pSV40 (25 ug) in 100 ul buffer D with 25 units Bcl I for 60 minutes at 50° C., followed by the addition of 50 units Bam HI and additional incubation at 37° C. for 60 minutes. Plasmid pDHFR' was linearized with Bam HI and treated with calf intestinal phosphatase. DNA fragments were resolved by agarose gel electrophoresis, and the 4.9 kb pDHFR' fragment and 0.2 kb SV40 fragment were isolated. These fragments (200 ng pDHFR' DNA and 100 ng SV40 DNA) were incubated in 10 ul buffer C containing 100 units $T_4$ polynucleotide ligase for 4 hours at 12° C., and the resulting construct (pD1) used to transform *E. coli* RR1.

Plasmid pD1 was modified by deleting the "poison" sequences in the pBR322 region (Lusky and Botchan, *Nature* 293: 79–81, 1981). Plasmids pD1 (6.6 ug) and pML-1 (Lusky and Botchan, ibid) (4 ug) were incubated in 50 ul buffer A with 10 units each Eco RI and Nru I for 2 hours at 37° C., followed by agarose gel electrophoresis. The 1.7 kb pD1 fragment and 1.8 kb pML-1 fragment were isolated and ligated together (50 ng each) in 20 ul buffer C containing 100 units $T_4$ polynucleotide ligase for 2 hours at 12° C., followed by transformation into *E. coli* HB101. Colonies containing the desired construct (designated ppD1) were identified by rapid preparation analysis. Ten ug of ppD1 was then digested with 20 units each Eco RI and Bgl II, in 50 ul buffer A for 2 hours at 37° C. . The DNA was electrophoresed through agarose, and the desired 2.8 kb fragment (fragment C) comprising the pBR322, 3' splice site and poly A sequences was isolated.

To generate the remaining fragments used in constructing pD5, pDHFRIII was modified to convert the Sac II (Sst II) site into either a Hind III or Kpn I site. Ten ug pDHFRIII were digested with 20 units Sst II for 2 hours at 37° C., followed by phenol extraction and ethanol precipitation. Resuspended DNA was incubated in 100 ul buffer B containing 10 mM dCTP and 16 units $T_4$ DNA polymerase for 60 minutes at 12° C., phenol extracted, dialyzed, and ethanol precipitated. DNA (5 ug) was ligated with 50 ng kinased Hind III or Kpn I linkers in 20 ul buffer C containing 400 units $T_4$ DNA ligase for 10 hours at 12° C., phenol extracted and ethanol precipitated. After resuspension in 50 ul buffer A, the resultant plasmids were digested with 50 units Hind III or Kpn I, as appropriate, and electrophoresed through agarose. Gel-isolated DNA (250 ng) was ligated in 30 ul buffer C containing 400 units $T_4$ DNA ligase for 4 hours at 12° C. and used to transform *E. coli* RR1. The resultant plasmids were designated pDHFRIII (Hind III) and pDHFRIII (Kpn I). A 0.4 kb Eco RI-Kpn I fragment (fragment A) was then purified from pDHFRIII (Kpn I) by digestion with Eco RI and Kpn I followed by agarose gel electrophoresis.

The SV40 enhancer sequence was inserted into pDHFRIII (Hind III) as follows: 50 ug SV40 DNA was incubated in 120 ul buffer A with 50 units Hind III for 2 hours at 38° C., and the Hind III C SV40 fragment (5171–1046 bp) was gel purified. Plasmid pDHFRIII (Hind III) (10 ug) was treated with 250 ng calf intestinal phosphatase for 1 hour at 37° C., phenol extracted and ethanol precipitated. The linearized plasmid (50 ng) was ligated with 250 ng of the Hind III C SV40 fragment in 16 ul buffer C for 3 hours at 12° C., using 200 units $T_4$ polynucleotide ligase, and transformed into *E. coli* HB101. A 0.9 kb Kpn I- Bgl II fragment (fragment B) was then isolated from this plasmid.

For the final construction of pD5, fragments A and B (50 ng each) were ligated with 10 ng fragment C with 200 units $T_4$ polynucleotide ligase for 4 hours at 12° C., followed by transfection of *E. coli* RRI. Positive colonies were detected by rapid plasmid preparation and endonuclease analysis, and a large-scale preparation of pD5 was made (FIG. 4).

Example 4B—Construction of pDX

The vector pDX was derived from pDll and pD5'. Plasmid pD5' is a vector identical to pD5 except that the SV40 polyadenylation signal (i.e., the SV40 Bam HI [2533 bp] to BclI [2770 bp] fragment) is in the late orientation (FIG. 4), Thus, pD5' contains a Bcl I site as the site of gene insertion. Plasmid pDll differs from pD5 in that the Hind III (5171 bp in the SV40 genome) to Kpn I (294 bp in SV40) fragment, containing enhancer sequences, is in the opposite orientation.

To generate pDX, the Eco RI site in pD11 was converted to a Bcl I site by Eco RI cleavage, incubation with S1 nuclease, and subsequent ligation with Bcl I linkers. DNA was prepared from a positively identified colony, and the 1.9 kb Xho I-Pst I fragment containing the altered restriction site was prepared via agarose gel electrophoresis. In a second modification, Bcl I-cleaved pD5' was ligated with kinased Eco RI-Bcl I adaptors (constructed from oligonucleotides ZC525, 5'GGAATTCT3' and ZC526, 5'GATCAGAATTCC3') in order to generate an Eco RI site as the position for inserting a gene into the expression vector. Positive colonies were identified by restriction endonuclease analysis, and DNA from this was used to isolate a 2.3 kb Xho I-Pst I fragment containing the modified restriction site. The two above-described DNA fragments were incubated together with $T_4$ DNA ligase, transformed into *E. coli* HB101 and positive colonies were identified by restriction analysis. A preparation of such DNA, termed pDX, was made.

Example 5—Expression of GM-CSF in BHK Cells

BHK tk⁻ts13 cells were transfected to express native GM-CSF and mutant GM-CSFs II and IV. Cultured cells were split by trypsin treatment, replated at 15% density and grown for 24 hours in DMEM supplemented with 10% heat inactivated fetal calf serum and 1% antibiotics. Ten ug of CsCl banded plasmid DNA (pDcGMI, pDcGMII or pDcGMIV) was co-precipitated with 1 ug of the plasmid DHFR$^{res}$-pD5' (a pD5-derived plasmid containing a methotrexate resistant DHFR gene [Levinson et al., EP 117,060]) and with 10 ug of sonicated salmon sperm DNA (as carrier). The mixture was resuspended in 1 ml of 2 ×Hebs buffer (1 gm HEPES, 1.6 gm NaCl, 0.07 gm KCl, 0.03 gm $Na_2HPO_4$—$2H_2O$ per 100 ml, pH 7.05). One ml of 250 mM $CaCl_2$ was added to the solution slowly while bubbling air through it and a DNA-calcium phosphate precipitate was formed. The precipitate was added to the 24 hour culture of the BHK cells and allowed to incubate for 4 hours. The culture supernatant was removed by aspiration and 2 ml of 15% glycerol in TBS (50 mM Tris pH 7.5, 150 mM NaCl) was added to the cells for two minutes. The glycerol solution was removed, the cells were rinsed in TBS without glycerol, and regular culture medium was added. After 3 days, culture supernatant was removed and assayed for biologically active GM-CSF and the cells were split by trypsin treatment to 10% confluence. The cells were then incubated in DMEM containing 10% heat inactivated, dialyzed fetal calf serum, 1% antibiotics and 250 nM methotrexate.

After 1 week of incubation, the medium was changed and the cells were incubated for an additional week. Individual colonies were then isolated with cloning cylinders and cells were removed by trypsin treatment. The cells were then incubated in 35 mm cultures in the same medium for 1 week, then split with trypsin into 100 mm plates. The cells were sequentially passaged by splitting to 10% confluence by trypsin treatment in the following conditions:

250 nM methotrexate×2

1 uM methotrexate×2

5 uM methotrexate×2

25 uM methotrexate×2

100 uM methotrexate×2

Following the last passage, the cells were grown to confluence in maxiplates in 100 uM methotrexate-containing medium and four plates were split into a Nunc 10 plate cell factory and grown to confluence. The cells were then transferred to DMEM supplemented with 0.5% fetal calf serum and 1% antibiotics.

Recombinant GM-CSFs I, II and IV were purified from BHK cell-conditioned media by a combination of immunoaffinity chromatography and high performance liquid chromatography.

A monoclonal antibody to GM-CSF was diluted with an equal volume of 2×TNEN (1M Tris pH 8.0, 5M NaCl, 250 mM EDTA, 10% NP-40) and the solution was centrifuged at 30,600×g for twenty minutes. The pellet was discarded and the supernatant was applied to a 10 ml protein A-Sepharose column which had been equilibrated in TNEN. The column was washed with 20 ml phosphate buffered saline (PBS) to remove unbound material. The column was eluted with 0.1M sodium citrate pH 3.0 and collected fractions were neutralized to pH 7.0 with Tris pH 8.8. Peak fractions, as determined by cellulose acetate electrophoresis, were pooled and dialyzed against 0.1M NaHCO$_3$, 0.5M NaCl pH 8.3. Protein yield was determined by absorbance at 280 nm.

A 20 ml immunoaffinity column was prepared by coupling 50 mg of purified antibody to CnBr-activated Sepharose (Pharmacia, Inc., Piscataway, N.J.) using conditions specified by the manufacturer.

GM-CSF proteins were purified from concentrated media. Approximately 12 l of medium was concentrated to approximately 400 ml using an Amicon RA2000 concentrator. The concentrate was applied to the immunoaffinity column and the column was washed with 30 ml of PBS containing 0.5 M NaCl. Bound material was eluted from the column with 0.1 M glycine pH 2.5. Protein-containing fractions were pooled.

The affinity-purified GM-CSF was further purified by HPLC. The pooled material was loaded onto a C-4 column and eluted at a rate of 1 ml/minute using a gradient of 100% A (0.1% trifluoroacetic acid [TFA] in H$_2$O) at time 0 to 70% B (0.1% TFA in acetonitrile)/30% A at 35 minutes. Elution was monitored at 280 nm. Peak fractions were lyophilized and stored at −80° C. and aliquots were assayed by electrophoresis on 12% polyacrylamide gels. Lyophilized peak fractions identified from the gel were redissolved in 10 mM acetic acid, pooled, aliquoted, lyophilized and stored at −80° C.

Example 6—Pharmacokinetics of Recombinant GM-CSF

Purified native (cGMI), O-linked carbohydrate-containing (cGMII) and carbohydrate-deficient (cGMIV) forms of recombinant human GM-CSF from transfected BHK cells were tested in baboons for circulating half-life and effects on blood cell counts.

Three baboons were selected for study. To eliminate experimental error due to individual variations in metabolism, each animal was tested with each form of the protein at 5, 20, or 80 μg/kg at one week intervals. In a second set of experiments the same animal was given all three dose levels of the same preparation one week apart. This experimental design is set forth in Table IV.

TABLE IV

| Animal | 1 | 2 | 3 |
|---|---|---|---|
| Week 1 | 5 μg/kg I | 20 μg/kg I | 80 μg/kg I |
| Week 2 | 5 μg/kg II | 20 μg/kg II | 80 μg/kg II |
| Week 3 | 5 μg/kg IV | 20 μg/kg IV | 80 μg/kg IV |
| Week 4 | 5 μg/kg I | 5 μg/kg II | 5 μg/kg IV |
| Week 5 | 20 μg/kg I | 20 μg/kg II | 20 μg/kg IV |
| Week 6 | 80 μg/kg I | 80 μg/kg II | 80 μg/kg IV |

For administration, HPLC-purified GM-CSF (Example 5) was diluted in autologous serum which had been heat-inactivated by treatment at 56° C. for 30 minutes. Animals were given a bolus injection over a one minute period.

Figure 6A:
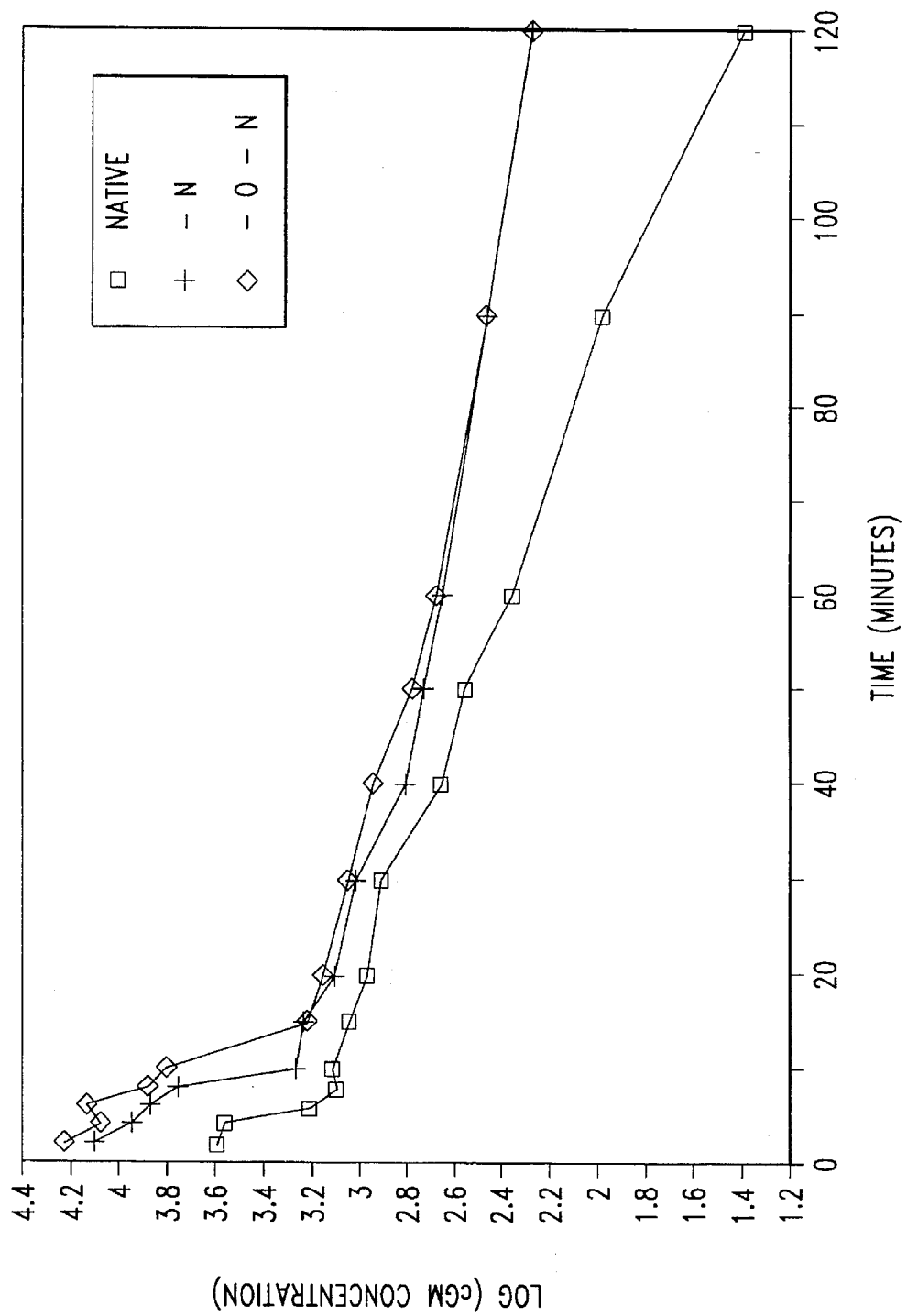
FIGS. 6A, B and C illustrate the results of pharmacokinetic studies of recombinant GM-CSFs in baboons.
Figure 6B:
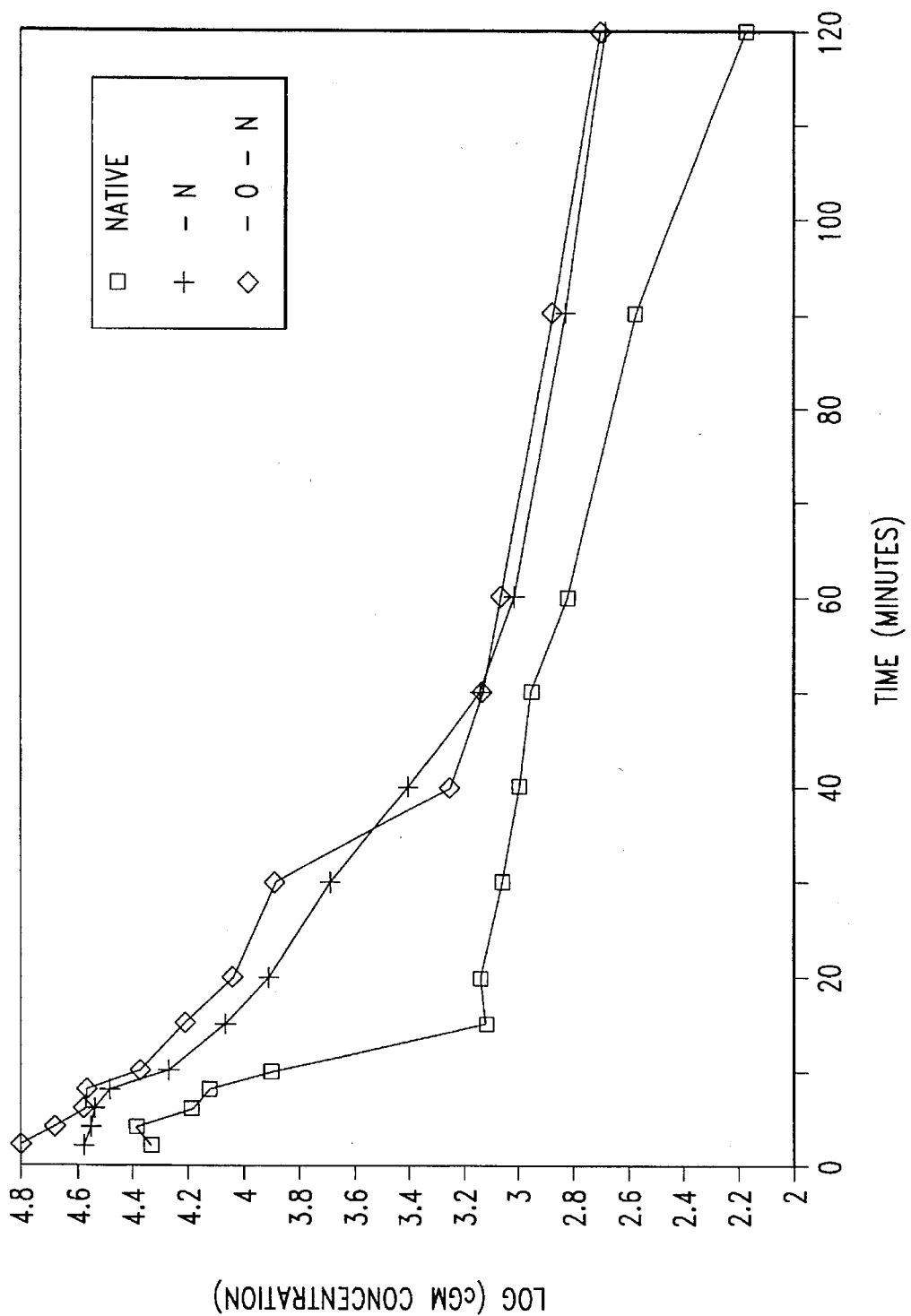
Figure 6C:
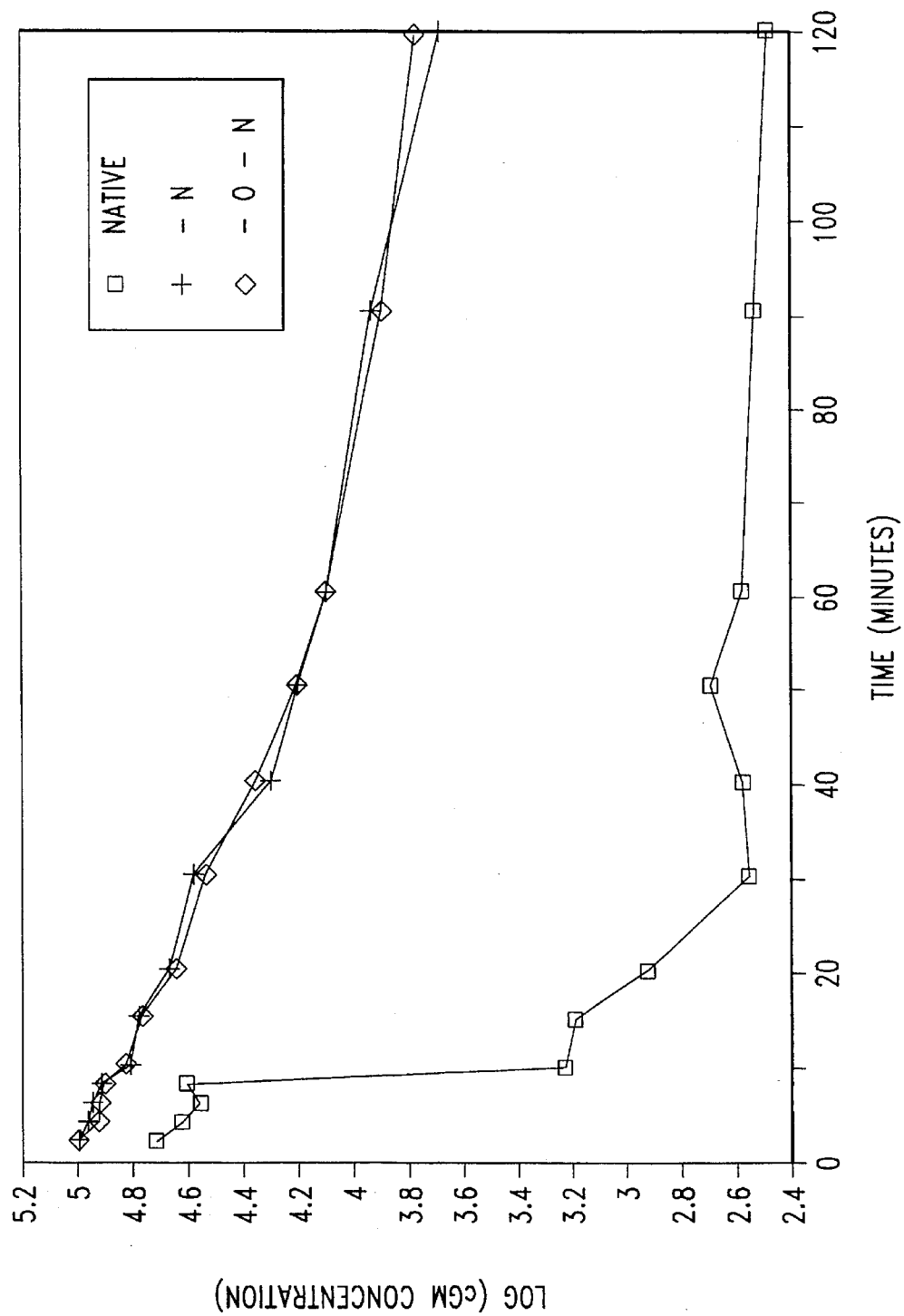

To determine the half-live of the protein in the circulation, one cc plasma samples were obtained at 2, 4, 6, 8, 10, 15, 20, 30, 40, 50, 60, 90, and 120 minutes after injection and GM-CSF concentration was measured by radioimmune assay. Murine monoclonal antibody to GM-CSF was diluted to 2.5 μg/ml in Buffer A (0.1M Na$_2$CO$_3$ pH 9.6, 0.02% NaN$_3$) and 100 μl of this solution was added to each well of a 96-well microtiter plate. The plates were incubated at 37° C. for at least 1.5 hour, then washed three times with 150 μl/well Buffer C (PBS containing 0.05% Tween-20, 0.02% NaN$_3$). The wells were then blocked by adding 200 μl Buffer B (PBS containing 2% bovine serum albumin, 0.05% Tween-20, 0.02% NaN$_3$) and the plates were incubated at 37° C. for at least 1.5 hours. The buffer was removed and the wells were washed three times with 150 μl Buffer C. Samples (10 μl plus 90 μl Buffer B) were then added and the plates were incubated at 37° C. for at least 1 hour. The solution was removed and the plates were washed three times with Buffer C. A second murine anti-GM-CSF monoclonal antibody labeled with $^{125}$I was then added at 100,000 cpm/well and the plates were incubated at 37° C. for at least 1 hour. The solution was removed, the wells were washed three times with Buffer C and counted in a gamma counter. Results, shown in FIGS. 6A, B and C, indicated that the mutant forms of GM-CSF have an increased half-life in the circulation, particularly at the higher doses.

We claim:

1. A method for producing a human GM-CSF protein having higher specific activity than native human GM-CSF, comprising:

introducing into a eucaryotic host cell an expression unit comprising a promoter followed downstream by a DNA sequence encoding a human GM-CSF protein lacking N-linked glycosylation but having O-linked glycosylation, said protein having higher specific activity than native human GM-CSF;

growing said eucaryotic host cell in an appropriate medium; and isolating the protein product encoded by said DNA sequence and produced by said eucaryotic host cell.

2. A method according to claim 1 wherein said host cell is a *Saccharomyces cerevisiae* cell.

3. A method according to claim 1 wherein said protein comprises the amino acid sequence of FIG. 1, starting with alanine, number 18, and ending with glutamate, number 144.

4. A method for producing a human GM-CSF protein having higher specific activity than native human GM-CSF, comprising:

introducing into a eucaryotic host cell an expression unit comprising a promoter followed downstream by a DNA sequence encoding a human GM-CSF protein lacking N-linked and O-linked glycosylation, said protein having higher specific activity than native human GM-CSF;

growing said eucaryotic host cell in an appropriate medium; and isolating the protein product encoded by said DNA sequence and produced by said eucaryotic host cell.

5. A method according to claim 4 wherein said protein comprises the amino acid sequence of FIG. 2, starting with alanine, number 18, and ending with glutamate, number 144.

6. A method according to claim 4 wherein said host cell is a *Saccharomyces cerevisiae* cell.

* * * * *